United States Patent [19]
Imasato et al.

[11] Patent Number: 5,600,570
[45] Date of Patent: Feb. 4, 1997

[54] METHOD AND APPARATUS FOR MODELING SYNTHETIC CRYSTAL STRUCTURE

[75] Inventors: Yutaka Imasato, Chiba; Masahito Kawai, Kawasaki, both of Japan

[73] Assignee: Fujitsu Ltd., Kawasaki, Japan

[21] Appl. No.: 846,335

[22] Filed: Mar. 6, 1992

[30] Foreign Application Priority Data

Mar. 8, 1991 [JP] Japan .................................. 3-043843

[51] Int. Cl.$^6$ ....................................... G06F 17/00
[52] U.S. Cl. .......................................... 364/496; 364/499
[58] Field of Search ........................... 364/149, 150, 364/151, 468, 192, 496, 497, 499, 578; 156/600, 603; 395/118, 135, 137, 139, 140, 141

[56] References Cited

U.S. PATENT DOCUMENTS

| | | | |
|---|---|---|---|
| 4,642,762 | 2/1987 | Fisanick | 364/300 |
| 4,881,175 | 11/1989 | Ladner | 364/496 |
| 4,951,231 | 8/1990 | Dickinson et al. | 395/135 X |
| 5,025,388 | 6/1991 | Cramer, III et al. | 364/496 |
| 5,038,218 | 8/1991 | Matsumoto | 395/137 X |
| 5,056,035 | 10/1991 | Fujita | 364/497 |
| 5,265,197 | 11/1993 | Kondo | 364/192 X |

*Primary Examiner*—Roy N. Envall, Jr.
*Assistant Examiner*—Brian C. Oakes
*Attorney, Agent, or Firm*—Staas & Halsey

[57] ABSTRACT

A method for modeling a synthetic crystal structure formed of a first crystal structure and a second crystal structure by representing the first crystal structure using a first coordinate system and the second crystal structure using a second coordinate system, specifying a first atom, a first lattice and a first crystal face of the first crystal structure, the first crystal face including the first atom and the first lattice; specifying a second atom, a second lattice and a second crystal face of the second crystal structure the second crystal face including the second atom and the second lattice; transforming the second crystal structure system represented by the second coordinate system into a second crystal structure represented by the first coordinate system so that an assembling condition is satisfied, the assembling condition being defined as a condition in which the second atom, the second lattice and the crystal face of the second crystal structure are respectively superposed on the first atom, the first lattice and the first crystal face of the first crystal structure; and adding the second crystal structure represented by the first coordinate system to the first crystal structure, so that a synthetic crystal structure formed of the first and second crystal structures represented by the first coordinate system, is obtained.

10 Claims, 11 Drawing Sheets

MAIN-CRYSTAL STRUCTURE

FIG. 5B

SUB-CRYSTAL STRUCTURE

METHOD AND APPARATUS FOR MODELING SYNTHETIC CRYSTAL STRUCTURE

BACKGROUND OF THE INVENTION

1. Field of the Invention

The present invention generally relates to a method and an apparatus for modeling a synthetic crystal structure, and more particularly to a method and an apparatus for modeling a synthetic crystal structure which are used for designing inorganic materials in the fields of chemistry and physics, for example.

2. Description of Related Art

In a design of inorganic materials, such as superconductive materials and semiconductors, a modeling of a crystal structure represented by atoms is performed, and various structural data are extracted from a modeled crystal structure. Due to symmetry, periodicity of the modeled crystal structure, and to arrangement of atoms, physical functions of the designed inorganic material can be known. The crystal structure of an inorganic material is formed by synthesizing various featured structure elements. Thus, the various featured structure elements are synthesized so that virtual crystal structure is made. The physical functions of an inorganic material having the virtual crystal structure are then studied.

Conventionally, the modeling of a crystal structure of an inorganic material is carried out by operations of assembling plastic model of structure elements and tracing the assembled structure. In this conventional modeling of the crystal structure, as an operator actually assembles the plastic models of the structure elements by hand, it is hard for the operator to assemble the plastic models of the structure elements.

SUMMARY OF THE INVENTION

Accordingly, a general object of the present invention is to provide a novel and useful method and apparatus for modeling a synthetic crystal structure in which the disadvantages of the aforementioned prior art are eliminate.

a more specific object of the present invention is to provide a method and apparatus for modeling a synthetic crystal structure in which the modeling of a synthetic crystal structure can be easily carried out.

The above objects of the present invention are achieved by a method for modeling a synthetic crystal structure formed of a first crystal structure having a plurality of atoms and lattices and a second crystal structure having a plurality of atoms and lattices, the method comprising the steps of: (a) representing the first crystal structure by using a first coordinate system and the second crystal structure by using a second coordinate system; (b) specifying a first atom, first lattice and a first crystal face of the first crystal structure, the first crystal face including the first atom and the first lattice; (c) specifying a second atom, a second lattice and a second crystal face of the second crystal structure, the second crystal structure including the second atom and the second lattice; (d) transforming the second crystal structure system represented by the second coordinate system into a second structure represented by the first coordinate system so that an assembling condition is satisfied, the assembling condition being defined as a condition in which the second atom, the second lattice and the crystal face of the second crystal structure are superposed on the first atom, the first lattice and the first crystal face of the first crystal structure; and (e) adding the second crystal structure represented by the first coordinate system to the first crystal structure represented in step (a), so that a synthetic crystal structure formed of the first and second crystal structures represented by the first coordinate system is obtained.

The above objects of the present invention are also achieved by an apparatus for modeling a synthetic crystal structure formed of a first crystal structure having a plurality of atoms and lattices and a second crystal structure having a plurality of atoms and lattices, the apparatus comprising: selection means for selecting first data corresponding to the first crystal structure and second data corresponding to the second crystal structure, the first data being represented by a first coordinate system, and the second data being represented by a second coordinate system; first specifying means, coupled to the selection means, for specifying a first atom, a first lattice and a first crystal face of the first crystal structure, the first crystal face including the first atom and the first lattice; second specifying means, coupled to the selection means, for specifying a second atom, a second lattice and a second crystal face of the second crystal structure, the second crystal face including the second atom and the second lattice; transformation means for transforming the second crystal structure system represented by the second coordinate system into a second crystal structure represented by the first coordinate system so that an assembling condition is satisfied, the assembling condition being defined as a condition in which the second atom, the second lattice and the crystal face of the second crystal structure are respectively superposed on the first atom, the first lattice and the first crystal face of the first crystal structure; and display means for displaying second crystal structure, obtained by the transformation means, along with the first crystal structure selected by the selection means, so that a synthetic crystal structure formed of the first and second crystal structures represented by the first coordinate system is displayed by the display means.

According to the present invention, the first crystal structure and the second crystal structure are assembled into the synthetic crystal so that the assembling condition is satisfied, in which the second atom, the second lattice and the second crystal face of the second crystal structure are respectively superposed on corresponding parts of the first crystal structure. Thus, the synthetic crystal structure formed of the first and second crystal structures can be easily obtained.

Additional objects, features and modifications of the present invention will become apparent from the following detailed description when read in conjunction with the accompanying drawings.

DESCRIPTION OF THE PREFERRED EMBODIMENTS

A description will now be given of the principle of a modeling system according to an embodiment of the present invention.

Figure 1:
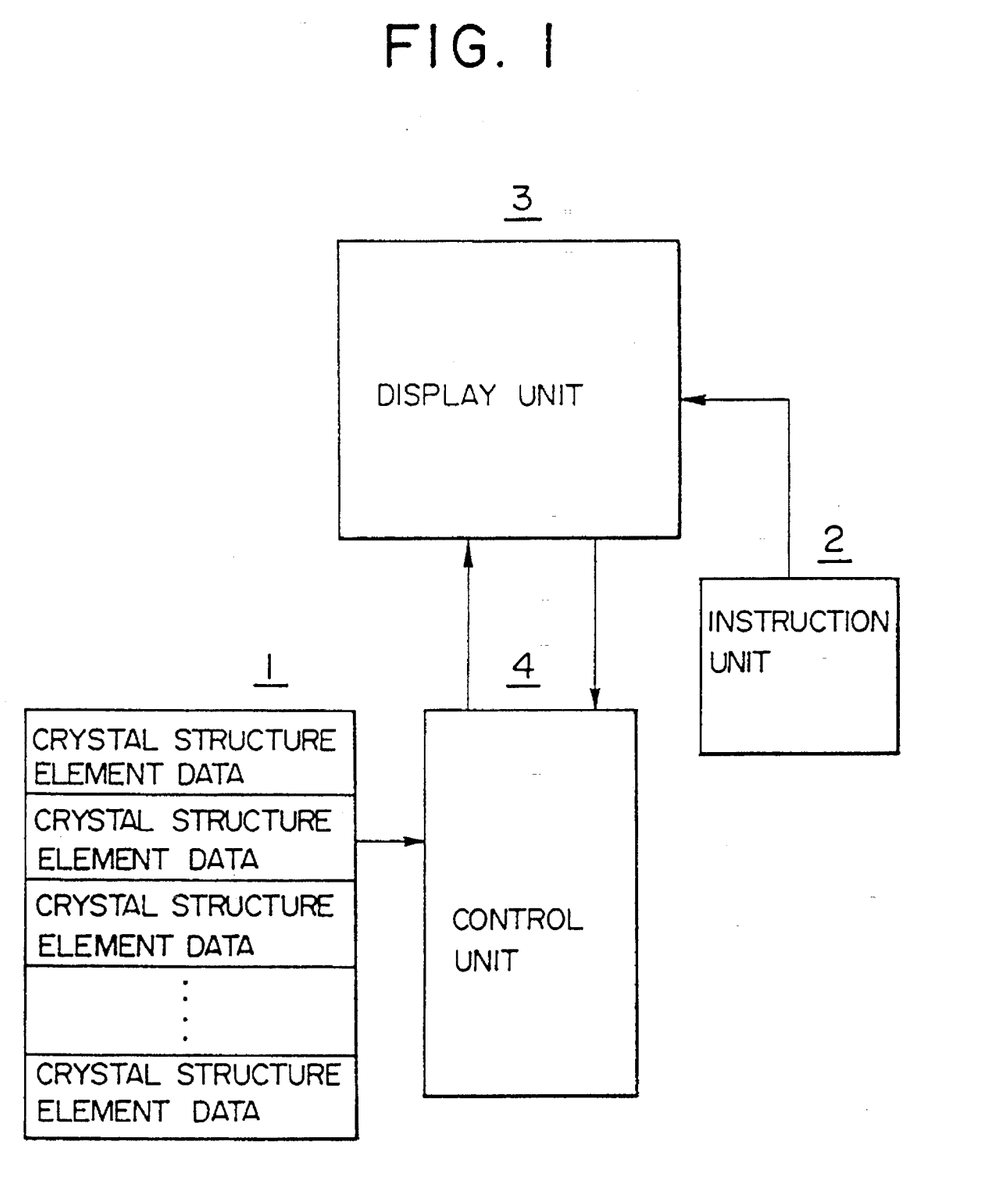
FIG. 1 is a block diagram illustrating an essential construction of a modeling system according to an embodiment of the present invention.

Referring to FIG. 1, which shows an essential structure of a modeling system, the modeling system has a memory unit 1, an instruction unit 2, a display unit 3 and a control unit 4. The memory unit 1 stores crystal structure element data representing each of structure units which can form various crystal structures. The control unit 4 reads out first and second crystal structure element data from the memory unit 1, and supplies them to the display unit 3. The display unit 3 displays a first crystal structure represented by the first crystal structure element data as a main-crystal structure, and a second crystal structure represented by the second crystal structure element data as a sub-crystal structure. An operator inputs, from the instruction unit 2, information representing crystal faces, crystal lattices and atoms of the main-crystal structure and the sub-crystal structure. The control unit 4 processes coordinate data representing the sub-crystal structure so that the input crystal face, crystal lattice and atom of the sub-crystal structure are superposed on input corresponding parts of the main-crystal structure. As a result, the sub-crystal structure is coupled to the main-crystal structure, so that a synthetic crystal into which the main-crystal structure and the sub-crystal structure are assembled is displayed on the display unit 3.

The main-crystal structure and the sub-crystal structure are assembled in accordance with the following rules (1)–(3).

(1) A superposed crystal face is one of six crystal faces in each of the main-crystal and sub-crystal structures. The superposed crystal face is communized by the sub-crystal structure and the main-crystal structure.

(2) One of the lattices i the sub-crystal structure is superposed on one of the lattices i the main-crystal structure.

(3) One of the atoms in the sub-crystal structure is superposed on one of the atoms in the main-crystal structure.

When the sub-crystal structure and the main-crystal structure are assembled in accordance with the above rules, a position of each lattice, a direction in which each lattice extends, and a position of each atom of the sub-crystal structure are equal to corresponding those of the main-crystal structure, on the superposed crystal face. That is, the coordinate data representing each lattice and each atom in the sub-crystal structure becomes the same as data in corresponding parts of the main-crystal structure, on the superposed crystal face.

A description will now be given of an embodiment of the present invention.

Figure 2:
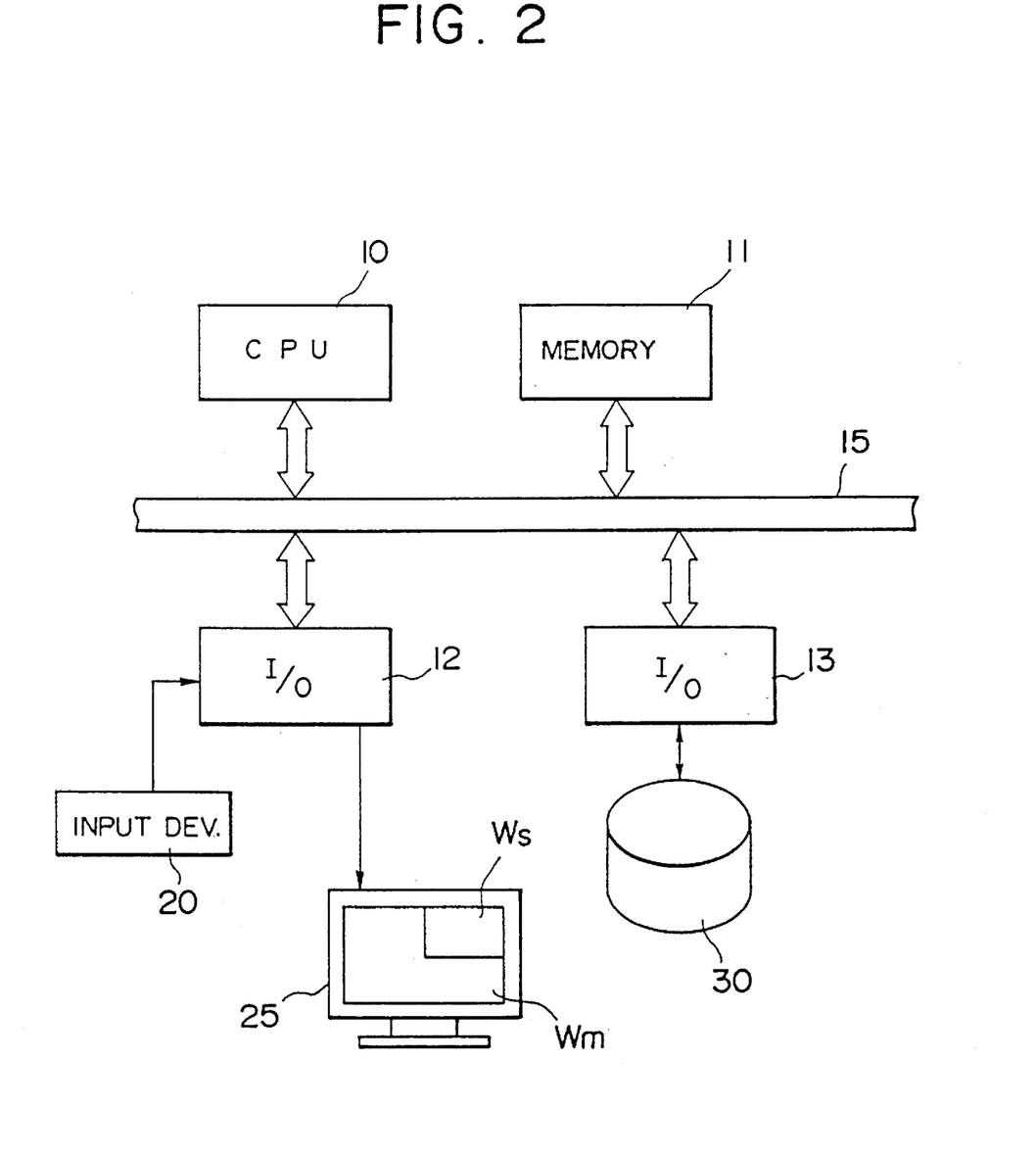
FIG. 2 is a block diagram illustrating a modeling system.

FIG. 2 shows a modeling system according to an embodiment of the present invention. Referring to FIG. 2, the modeling system has a CPU 10 (Central Processing Unit), a memory 11 and interface circuits 12 and 13, all coupled to each other by a system bus 15. The interface circuit 12 is coupled to an input device 20, such as a key board and a mouse, and a display device 25. The other interface circuit 13 is coupled to a storage unit 30, such as a disk unit. Instruction data input from the input device 20 is supplied to the CPU 10 via the interface circuit 12 and the system bus 15. Display data is supplied from the CPU 10 to the display device 25 via the system bus 15 and the interface circuit 12. Crystal structure element data, representing each of crystal structure units which can form various crystal structures, has been previously stored in the storage unit 30. A main-window Wm and a sub-window Ws can be set in the display device 25.

Figure 3:
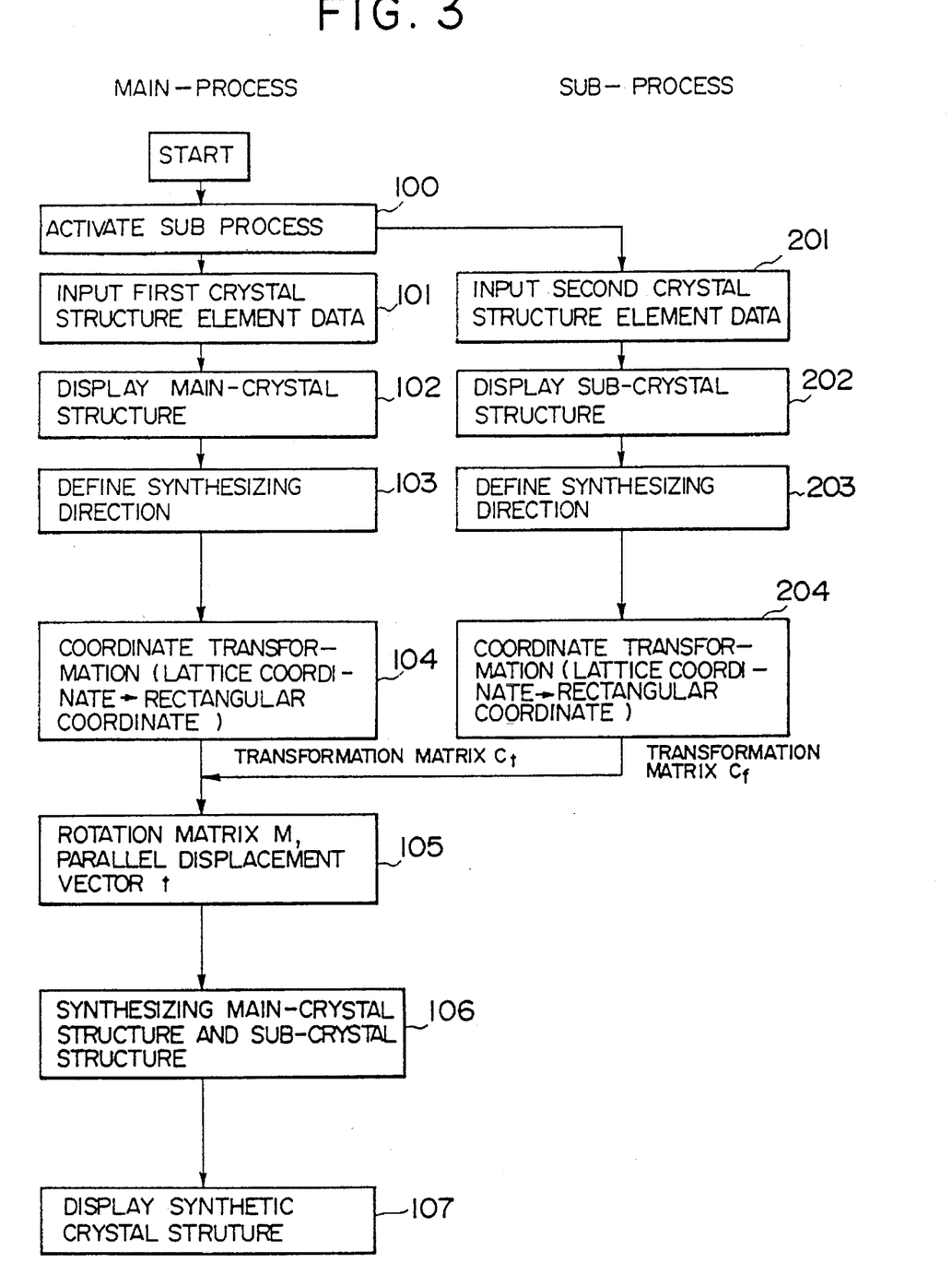
FIG. 3 is a flow chart illustrating a process for modeling a synthetic crystal.

The CPU 10 carries out a process for assembling two different crystal structures in accordance with a flow chart shown in FIG. 3, so that a synthetic crystal structure formed of the two crystal structure elements is displayed on the display device 25.

Figure 4:
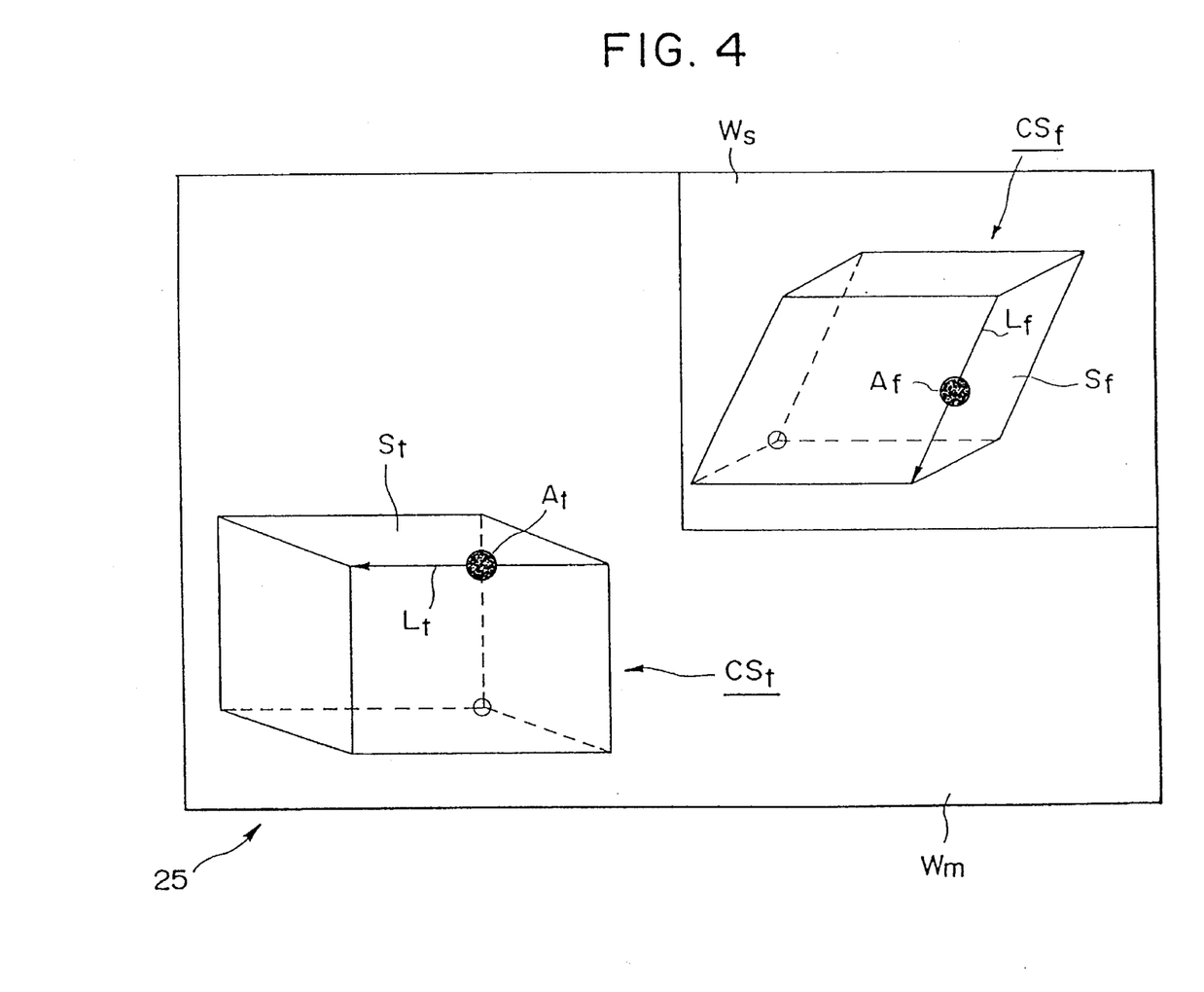
FIG. 4 is a diagram illustrating a display device displaying a main-crystal structure and a sub-crystal structure prior to being assembled.

When an operator inputs instructions for synthesizing different crystal structures and specifies a main-crystal structure and a sub-crystal structure from the input device 20, a main-process shown in FIG. 3 starts. In the main-process for processing the main-crystal structure, step 100 activates a sub-process for processing the sub-crystal structure. After the sub-process is activated, step 101 inputs first crystal structure element data, corresponding to the specified main-crystal structure, from the storage unit 30. The first crystal structure element data includes lattice constants (a, b, c, $\chi$, $\beta$, $\tau$) representing the main-crystal structure and coordinates [Fi=(pi, qi, ri)] representing a position of each atom (i) of the main-crystal structure. The coordinates (pi, qi, ri) are described by a lattice coordinate system set in the main-crystal structure. When the first crystal structure element data is read out from the storage unit 30, step 102 supplies display data corresponding to the first crystal structure element data to the display device 25, so that the main-crystal structure CSt is displayed in the main-window Wm on the display device 25, as shown in FIG. 4.

In the sub-process activated by the main-process, step 201 inputs second crystal structure element data, corresponding to the specified sub-crystal structure, from the storage unit 30. The second crystal structure element data includes lattice constants (a', b', c', $\alpha$', $\beta$', $\tau$') representing the sub-crystal structure and coordinates [Tj=(sj, tj, uj)] representing a position of each atom (j) of the sub-crystal structure in a lattice coordinate system. The coordinates are described by a lattice coordinate system set in the sub-crystal structure. After the second crystal structure element data is readout from the storage unit 30, step 202 supplies display data corresponding to the second crystal structure element data to the display device 25, so that the sub-crystal structure CSf is displayed in the sub-window Ws on the display device 25, as shown in FIG. 4.

In a state where the main-crystal structure CSt and the sub-crystal structure CSf are respectively displayed in the main-window Wm and the sub-window Ws on the display device 25, the operator specifies, by using the input device 20 (e.g. the mouse), an atom At, a lattice Lt and a crystal face St, in the main-crystal structure CSt, which should be superposed on corresponding those of the sub-crystal structure CSf. The operator also specifies the same things as the main-crystal structure CSt in the sub-crystal structure CSf by using the mouse. Tat is, an atom Af, a lattice Lf and a crystal face Sf to be superposed on corresponding those (At, Lt and St) of the main-crystal structure CSt are specified.

Figure 5A:
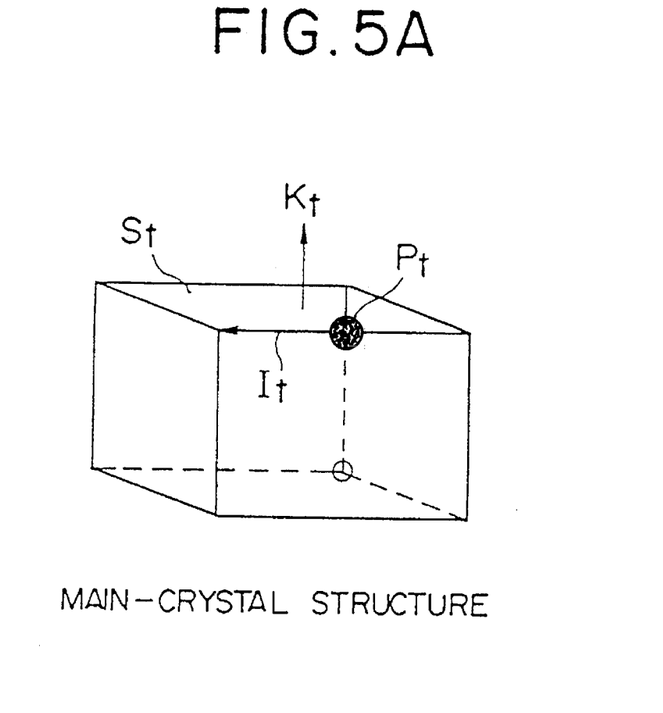
FIGS. 5a and 5b are diagrams illustrating coordinate transformation.
Figure 5B:
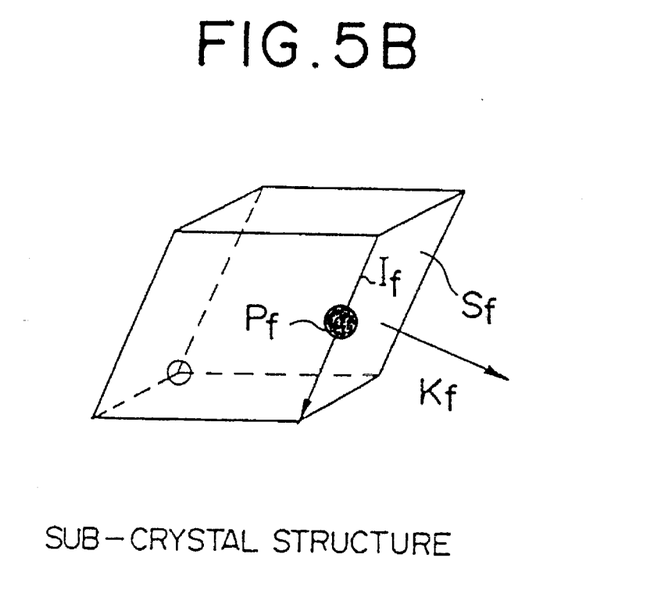

When the atom at, the lattice Lt and the crystal face St of the main-crystal structure CSt are specified, step 103, in the main-process, calculates a normal vector Kt of the crystal face St, a lattice vector It of the lattice Lt and a position Pt of the atom At, as shown in FIG. 5A. The normal vector Kt represents a direction perpendicular to the crystal face St. The lattice vector It represents a direction in which the lattice Lt extends. The normal vector Kt, the lattice vector It and the position Pt are described by the lattice coordinate system. Contrastingly, in the sub-process, when the atom Af, the lattice Lf and the crystal face Sf of the sub-crystal structure CSf are specified, step 203 calculates a normal vector Kf of the crystal face Sf, a lattice vector If of the lattice If and a position Pf of the atom Af in the same manner as step 103 in the main-process, as shown in FIG. 5B.

Figure 6:
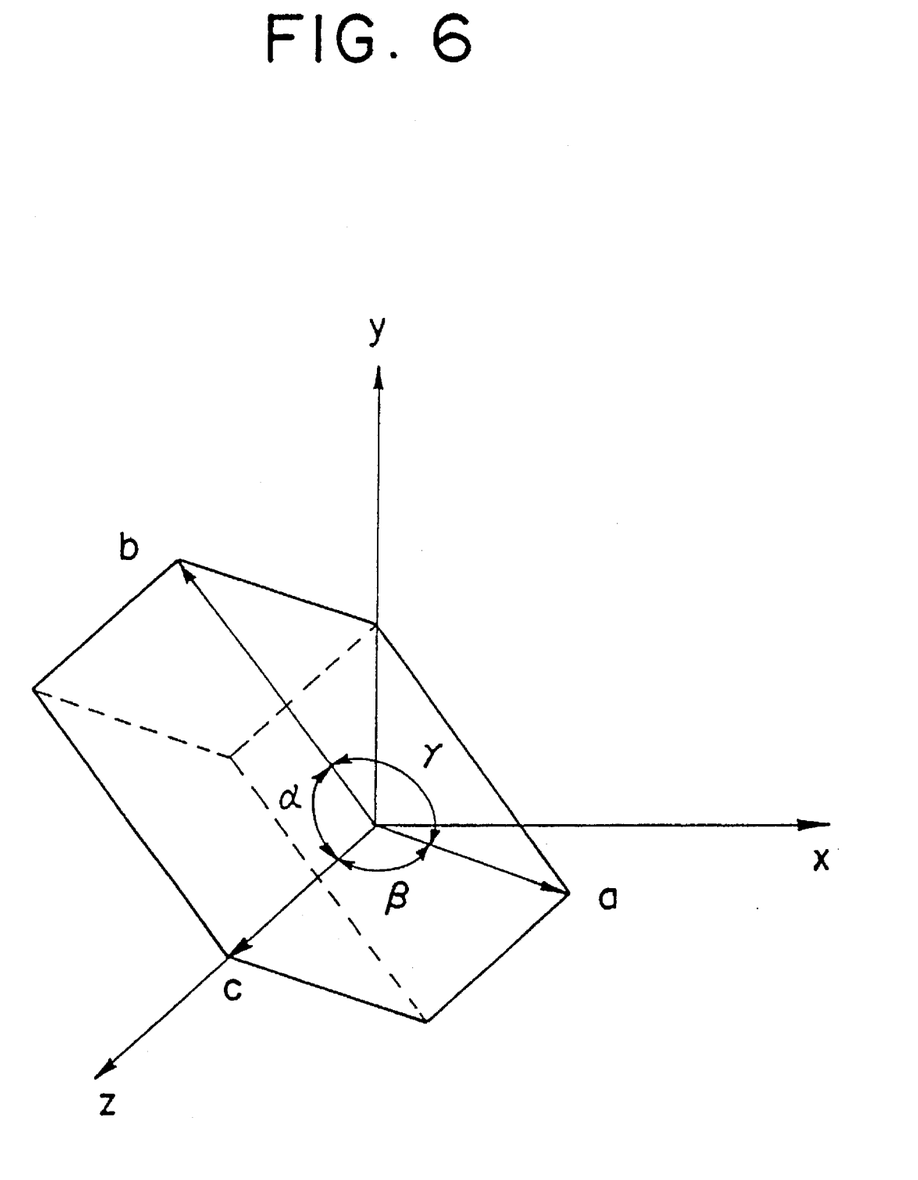
FIG. 6 is a diagram illustrating a relationship between a lattice coordinate system and a rectangular coordinate system.

After the above steps, step 104, in the main-process, carries out a coordinate transformation between the lattice coordinate system (a, b, c, $\chi$, $\beta$, $\tau$) and the rectangular coordinate system (x,y,z) shown in FIG. 6. That is, the normal vector Kt and the lattice vector It are respectively converted into new normal vector Vt and lattice vector Ut in accordance with the following formula, so that the new normal vector Vt and lattice vector Ut are described by the rectangular coordinate system $$X'=Ct\cdot X$$

where Ct is a transformation matrix, X is a vector described by the lattice coordinate system and X' is a vector described by the rectangular coordinate system. The transformation matrix Ct is defined as follows.

$$Ct = \begin{bmatrix} a\sin\alpha & 0 & a\cos\beta \\ \frac{b(\cos\gamma - \cos\alpha\cos\beta)}{\sin\beta} & b\left[1 - \cos\alpha - \frac{(\cos\gamma - \cos\alpha\cos\beta)^2}{\sin\beta}\right]^{\frac{1}{2}} & b\cos\alpha \\ 0 & 0 & 0 \end{bmatrix}$$

In the sub-process, the coordinate transformation is carried out, in the same manner as that in the main-process. That is, step 204 converts the normal vector Kf and the lattice vector If into new normal vector Vf and lattice vector Uf which are described by the rectangular coordinate system in accordance with the above formula. Step 204 also converts positions of all atoms of the sub-crystal structure CSf into new positions of the atoms described by the rectangular coordinate system. A position Sj of each atom (j) is denoted as Sj=(sj, tj, uj) in the rectangular coordinate system.

The normal vector Vf and the lattice vector Uf, described by the rectangular coordinate system, of the sub-crystal structure are transmitted from the sub-process to the main-process. The position data Sj, described by the rectangular coordinate system, of the sub-crystal structure is transmitted to the main-process. That is, the normal vector Vf, the lattice vector Uf and the position data Sj of each atom of the sub-crystal structure CSf are transmitted to and stored in the memory 11. The main-process assembles the main-crystal structure CSt and the sub-crystal structure CSf as follows.

Step 105 calculates a rotation matrix M ($\theta_x$, $\theta_y$, $\theta_z$) for rotating the sub-crystal structure so that the specified crystal face Sf and lattice Lf of the sub-crystal structure CSf are respectively superposed on the specified crystal face St and lattice Lt of the main-crystal structure CSt. The rotation matrix M ($\theta_x$, $\theta_y$, $\theta_z$) is obtained in accordance with the following conditions (1)–(5) between the normal vectors Vt and Vf and the lattice vectors Ut and Uf.

$$Vt=-Vf(=M\cdot Vf) \quad \ldots (1)$$

$$Ut=Uf(=M\cdot Uf) \quad \ldots (2)$$

$$Vt\ Ut=Vf\ Uf=0 \quad \ldots (3)$$

$$Vf=Uf=1 \quad \ldots (4)$$

$$Vt=Ut=1 \quad \ldots (5)$$

Condition (1) indicates that directions of the normal vectors Vt and Vf are opposite to each other. Condition (2) indicates that directions of the lattice vector Ut and Uf are equal to each other. Condition (3) indicates that the normal vector Vt and the lattice vector Ut are perpendicular to each other in the main-crystal structure CSt, and that the normal vector Vf and the lattice vector Uf are perpendicular to each other in the sub-crystal structure CSf. Conditions (4) and (5) indicate that the normal vectors Vt and Vf and the lattice vectors Ut and Uf are unit vectors, each having a unit length 1. The above conditions (1)–(5) correspond to the rules (1) and (2) described on page 6.

The rotation matrix M ($\theta_x$, $\theta_y$, $\theta_z$) is denoted as follows:

$$M = \begin{pmatrix} \cos\theta_x & -\sin\theta_x & 0 \\ \sin\theta_x & \cos\theta_x & 0 \\ 0 & 0 & 1 \end{pmatrix} \begin{pmatrix} \cos\theta_y & 0 & -\sin\theta_y \\ 0 & 1 & 0 \\ \sin\theta_y & 0 & \cos\theta_y \end{pmatrix} \begin{pmatrix} 1 & 0 & 0 \\ 0 & \cos\theta_z & -\sin\theta_z \\ 0 & \sin\theta_z & \cos\theta_z \end{pmatrix}$$

where $\theta_x$ is a rotation angle around an x-axis, $\theta_y$ is a rotation angle around a Y-axis and $\theta_z$ is a rotation angle around a z-axis.

Step 105 also calculates a parallel displacement vector t for displacing the sub-crystal structure in a predetermined direction so that the specified atom Af of the sub-crystal structure CSf is superposed on the specified atom At of the main-crystal structure CSt. The parallel displacement vector t is obtained in accordance with the following conditions (6) between the positions Pt and Pf.

$$t=Pt-Pf \quad \ldots (6)$$

The condition (6) indicates that the displacement between the atoms At and Af is t (=Pt-Pf).

After the rotation matrix M ($\theta_x$, $\theta_y$, $\theta_z$) and the parallel displacement vector t are obtained, step 106 carries out a coordinate transformation in accordance with the following formula:

$$Y = Ct^{-1}[M(\theta_x, \theta_y, \theta_z)X' + t]$$

where X' is position data described by the rectangular coordinate system, Y is position data described by the lattice coordinate system and $CT^{-1}$ is an inverse transformation matrix. That is, when the position data Sf (sj, tj, uj) of each atom of the sub-crystal structure CSf described by the rectangular coordinate system is substituted for X' in the above formula, new position data described by the lattice coordinate system in the main-window Wm on the display device 25 is obtained. Due to the calculation [M($\theta_x$, $\theta_y$, $\theta_z$) X'-t], the position data X' described by the rectangular coordinate system of the sub-crystal structure is converted into position data described by the rectangular coordinate system of the main-crystal structure. Due to the calculation $Ct^{-1}$, the position data described by the rectangular coordinate system is converted into the new position data described by the lattice coordinate system.

Figure 7:
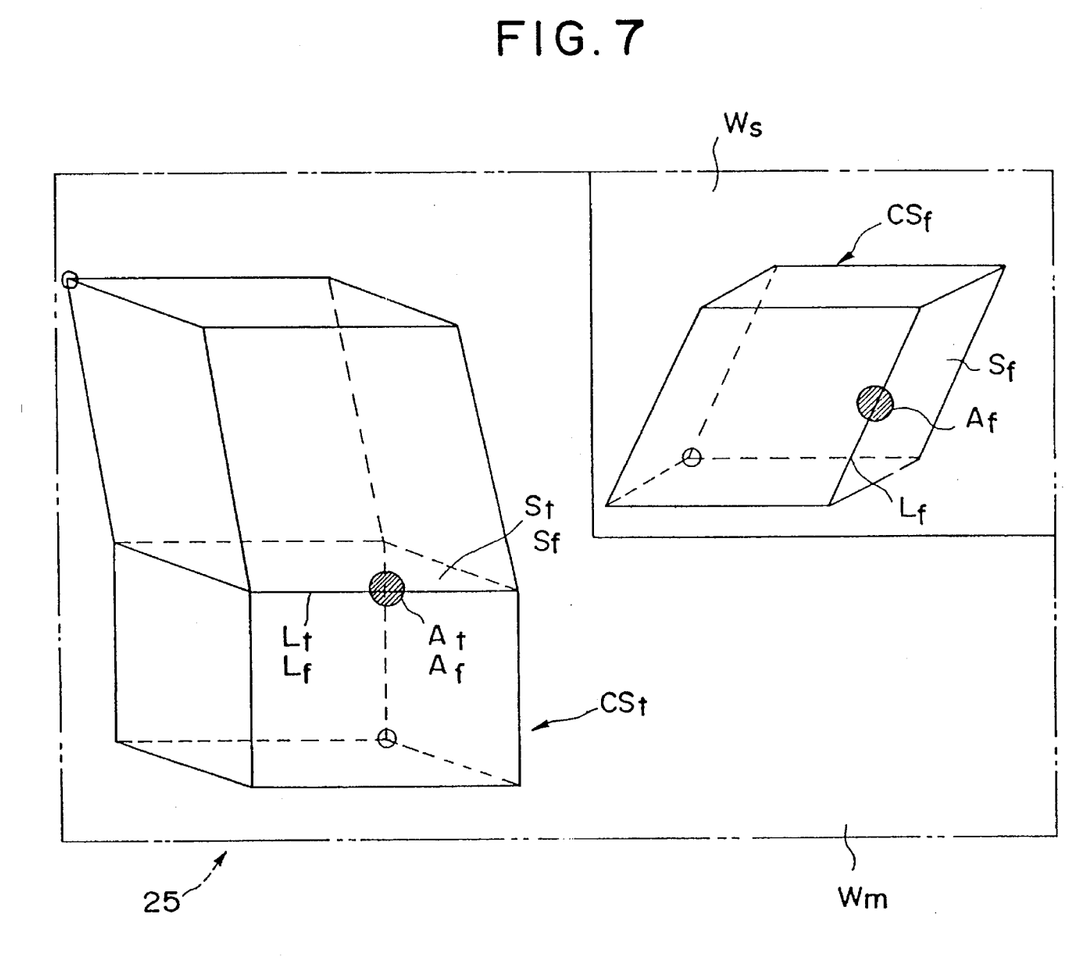
FIG. 7 is a diagram illustrating the display device displaying the main-crystal structure and the sub-crystal structure which have been assembled.

After this, step 107 supplies, to the display device 25, as display data, the position data of each atom of the sub-crystal structure CSf, obtained in accordance with the above formula. As a result, the sub-crystal structure CSf is displayed in the main-window Wm of the display device 25 in a state where the crystal face Sf, the lattice Lt and the atom At of the sub-crystal structure are respectively superposed on corresponding parts of the main-crystal structure CSt, as shown in FIG. 7. That is, the synthetic crystal structure formed of the main-crystal structure and the sub-crystal structure is displayed in the main-window Wm of the display device 25.

Figure 11:
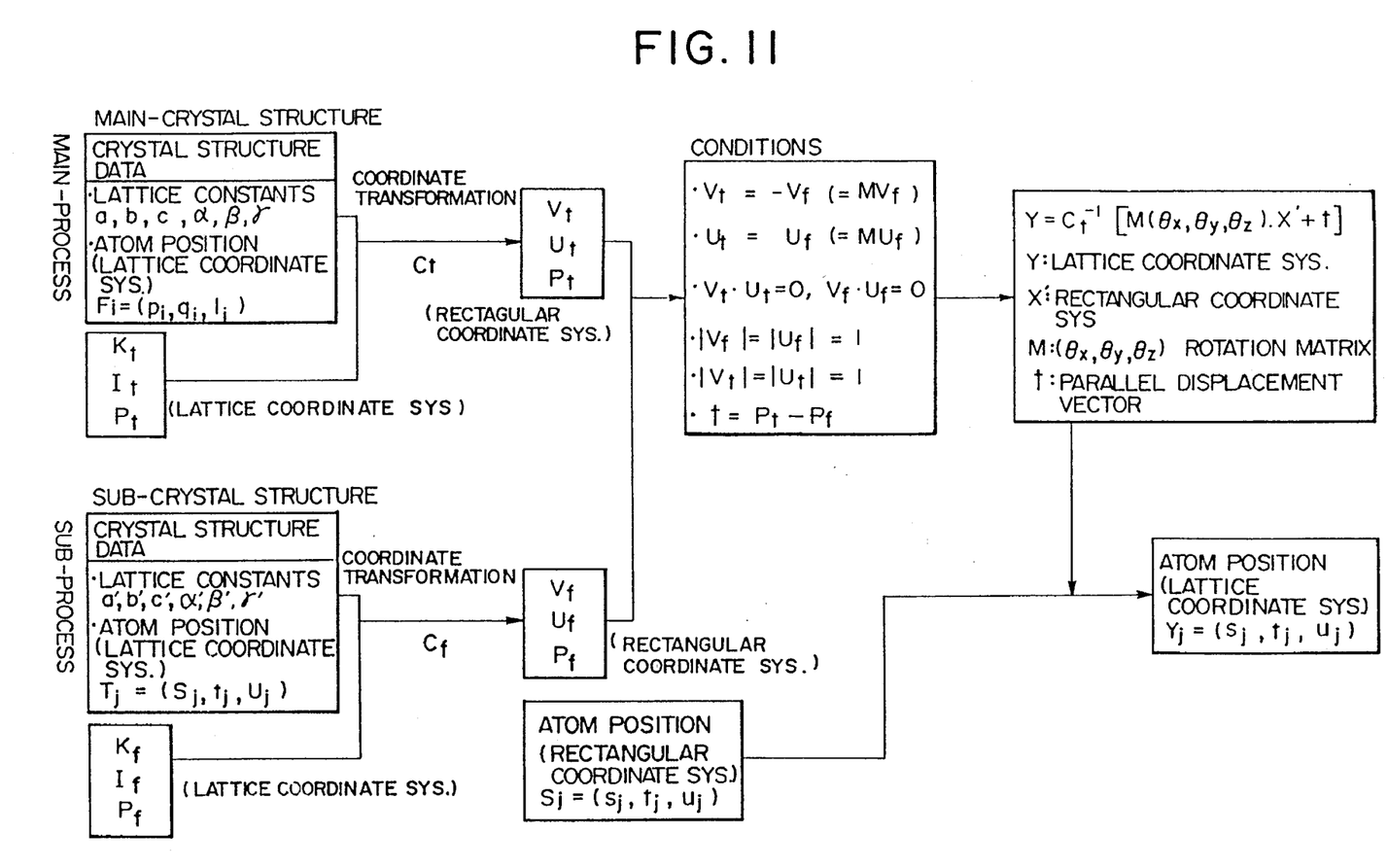
FIG. 11 is a flow chart illustrating changes in data representing the main-crystal structure and the sub-crystal structure are changed.

In the above processes, data representing the main-crystal structure and the sub-crystal structure are changed in accordance with flows shown in FIG. 11.

Figure 8:
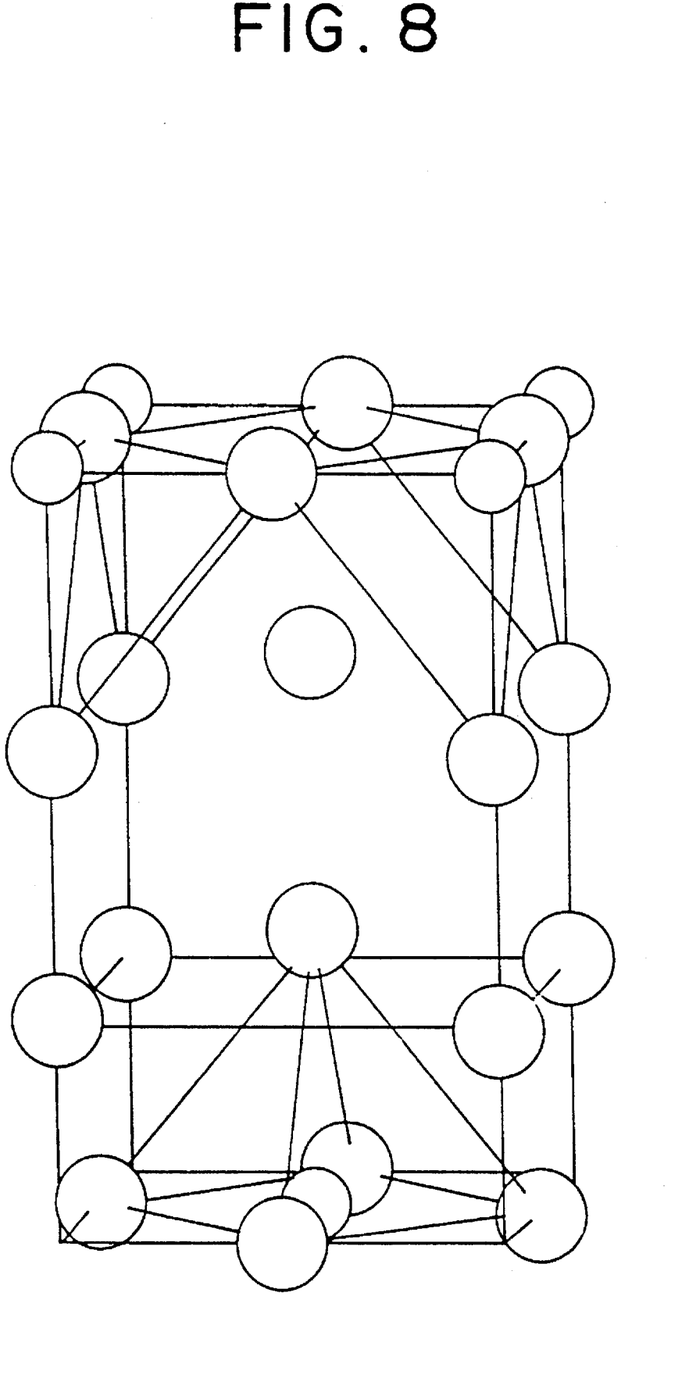
FIG. 8 is a diagram illustrating an embodiment of the sub-crystal structure.
Figure 9:
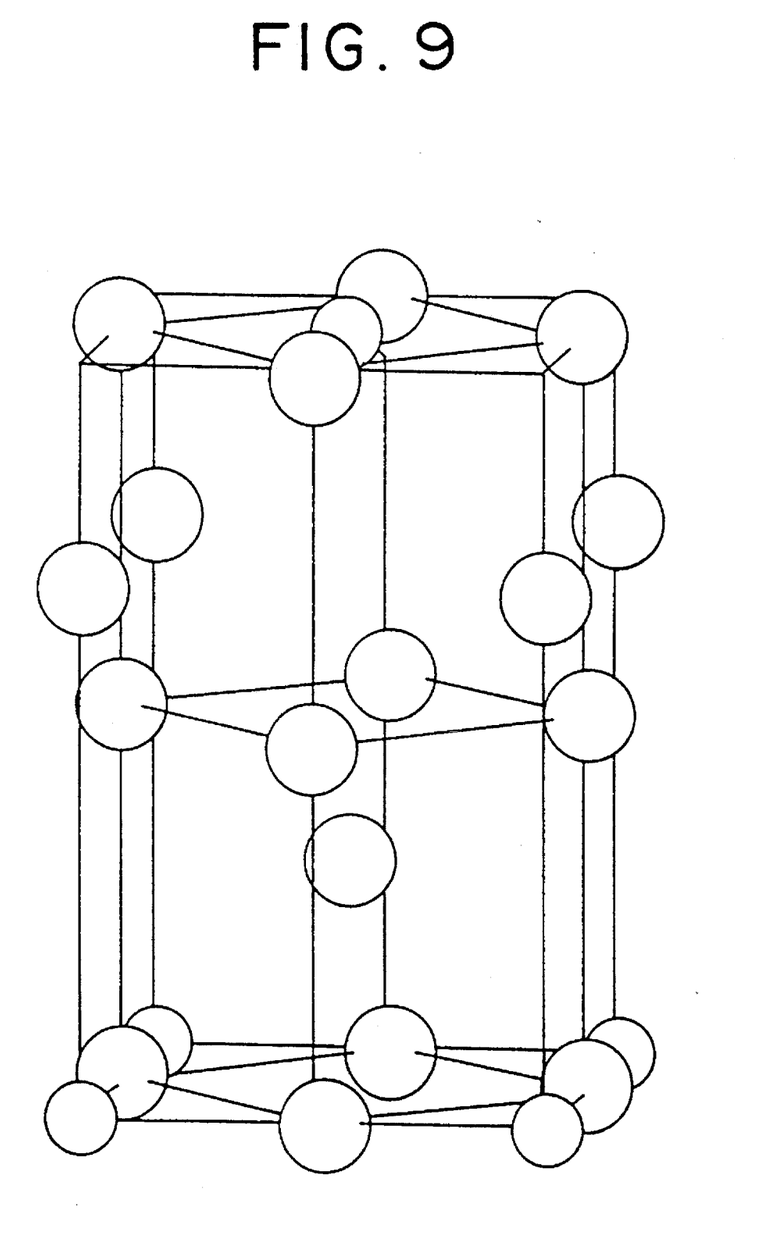
FIG. 9 is a diagram illustrating an embodiment of the main-crystal structure.
Figure 10:
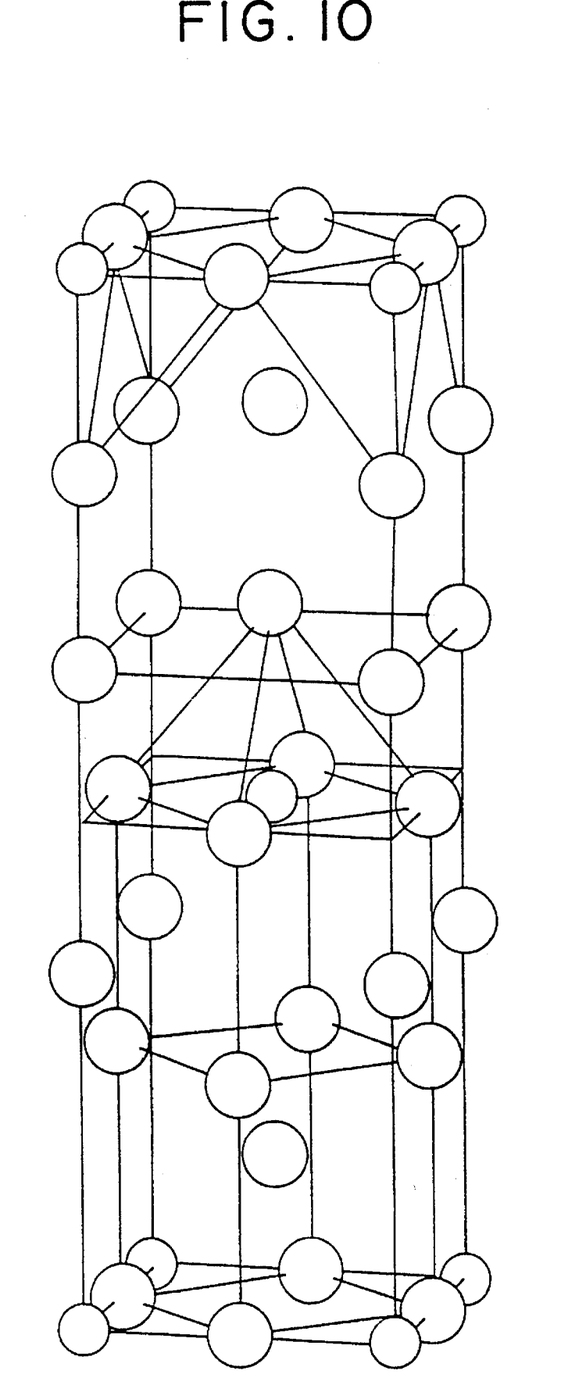
FIG. 10 is a diagram illustrating a synthetic crystal into which the main-crystal structure shown in FIG. 9 and the sub-crystal structure shown in FIG. 8 are assembled.

FIG. 8 shows a crystal structure of $La_2CuO_4$ including a NaCl type stacked structure. FIG. 9 shows a crystal structure of $Nd_2CuO_4$ including $CaF_2$ type stacked structure. When the crystal structure shown in FIG. 8 and the crystal structure shown in FIG. 9 are respectively supplied, as the sub-crystal structure and the main-crystal structure, to the above modeling system, a synthetic crystal structure shown in FIG. 10 is displayed in the main-window Wm of the display device 25.

In the above embodiment, data described by the the lattice coordinate system is converted into data described by the rectangular coordinate system. However, data described by the lattice coordinate system can be also converted into another coordinate system, such as a polar coordinate system.

The present invention is not limited to the aforementioned embodiments, and variations and modifications may be made without departing from the scope of the claimed invention.

What is claimed is:

1. A method for modeling a synthetic crystal structure formed from a first crystal structure having atoms on a first lattice, the first crystal structure being identified by a lattice coordinate system having lattice constants corresponding to the first crystal structure, and a second crystal structure having atoms on a second lattice, the second crystal structure being identified by a lattice coordinate system having lattice constants corresponding to the second crystal structure, said method comprising the steps of:

(a) specifying parts of the first crystal structure and parts of the second crystal structure to be superposed on each other, the parts of the first and second crystal structures being identified by the respective lattice coordinate systems;

(b) changing the coordinate system identifying the parts of the first crystal structure specified in step (a) from the lattice coordinate system having lattice constants corresponding to the first crystal structure to an intermediate coordinate system;

(c) changing the coordinate system identifying the second crystal structure, including the parts specified in step (a), from the lattice coordinate system having lattice constants corresponding to the second crystal structure to the intermediate coordinate system;

(d) calculating a movement operator for moving the second crystal structure so that the respective parts of the first and second crystal structures identified by the intermediate coordinate system are superposed on each other;

(e) moving the second crystal structure using the movement operator calculated in step (d);

(f) transforming the identification of the second crystal structure moved in step (e) from the intermediate coordinate system to the lattice coordinate system having lattice constants corresponding to the first crystal structure, and synthesizing a synthetic crystal structure formed from said first crystal structure and said second crystal structure, the synthetic crystal structure being identified by the lattice coordinate system having lattice constants corresponding to the first crystal structure; and (g) displaying said synthetic crystal structure synthesized in step (f).

2. The method as claimed in claim 1, wherein the parts of the first crystal structure specified in step (a) include an atom, a lattice edge of the first lattice and a first crystal face of said first crystal structure, the first crystal face including the atom and the lattice edge of the first lattice.

3. The method as claimed in claim 1, wherein the parts of the second crystal structure specified in step (a) include an atom, a lattice edge of the second lattice and a second crystal face of said second crystal structure, the second crystal face including the atom and the lattice edge of the second lattice.

4. The method as claimed in claim 1, wherein the intermediate coordinate system is a rectangular coordinate system.

5. The method as claimed in claim 1, wherein the movement operator calculated in step (d) includes a rotation operator for rotating said second crystal structure in the intermediate coordinate system and a parallel displacement operator for displacing said second crystal structure in a predetermined direction.

6. An apparatus for modeling a synthetic crystal structure formed from a first crystal structure having atoms on a first lattice, the first crystal structure being identified by a lattice coordinate system having lattice constants corresponding to the first crystal structure, and a second crystal structure having atoms on a second lattice, the second crystal structure being identified by a lattice coordinate system having lattice constants corresponding to the second crystal structure, said apparatus comprising:

first means for specifying parts of the first crystal structure and parts of the second crystal structure to be superposed on each other, the parts of the first and second crystal structures being identified by the respective lattice coordinate systems;

second means for changing the coordinate system identifying the parts of the first crystal structure specified by said first means from the lattice coordinate system having lattice constants corresponding to the first crystal structure to an intermediate coordinate system;

third means for transforming the identification of the second crystal structure, including the parts specified by said first means, from the lattice coordinate system having lattice constants corresponding to the second crystal structure to the intermediate coordinate system;

fourth means for calculating a movement operator for moving the second crystal structure so that the respective parts of the first and second crystal structures identified by the intermediate coordinate system are superposed on each other;

fifth means for moving the second crystal structure using the movement operator obtained by said fourth means;

sixth means for transforming the identification of the second crystal structure moved by said fifth means from the intermediate coordinate system to the lattice coordinate system having lattice constants corresponding to the first crystal structure, and synthesizing a synthetic crystal structure formed from said first crystal structure and said second crystal structure, the synthetic crystal structure being identified by the lattice coordinate system having lattice constants corresponding to the first crystal structure; and seventh means for displaying said synthetic crystal structure synthesized by said sixth means.

7. The apparatus as claimed in claim 6, wherein the parts of the first crystal structure specified by said first means includes an atom, a lattice edge of the first lattice and a first crystal face of said first crystal structure, the first crystal face including the atom and the lattice edge of the first lattice.

8. The apparatus as claimed in claim 6, wherein the parts of the second crystal structure specified by said first means include an atom, a lattice edge of the second lattice and a second crystal face of said second crystal structure, the second crystal face including the second atom and the lattice edge of the second lattice.

9. The apparatus as claimed in claim 6, wherein the intermediate coordinate system is a rectangular coordinate system.

10. The apparatus as claimed in claim 6, wherein the movement operator calculated by said fourth means includes a rotation operator for rotating said second crystal structure in the intermediate coordinate system and a parallel displacement operator for displacing said second crystal structure in a predetermined direction.

* * * * *

UNITED STATES PATENT AND TRADEMARK OFFICE
CERTIFICATE OF CORRECTION

PATENT NO. : 5,600,570
DATED : February 4, 1997
INVENTOR(S) : Yutaka IMASATO et al.

It is certified that error appears in the above-indentified patent and that said Letters Patent is hereby corrected as shown below:

<u>Col. 3,</u>　line 52, change "i" to --in--; and line 53, change "i" to --in--.

<u>Col. 4,</u>　line 34, change "$\chi$" to --$\alpha$--; and line 35, change "$\tau$" to --$\gamma$--.

<u>Col. 5,</u>　line 2, change "Tat" to --That--;

line 5, change "at" to --At--;

line 22, change "$\chi$" to --$\alpha$--, and change "$\tau$" to --$\gamma$--.

<u>In the Equation</u>:

line 1, center "0" in a middle column;

line 2, change "1 - cos$\alpha$ -" to --1 - cos$^2\alpha$ - --; and line 3, center "0" (second occurrence) in a middle column.

<u>Col. 6,</u>　line 63, change "tis" to --t is--.

<u>Col. 7,</u>　line 19, change "X' - t" to --X' + t--.

Signed and Sealed this

Twenty-second Day of July, 1997

Attest:

BRUCE LEHMAN

*Attesting Officer*　　　*Commissioner of Patents and Trademarks*